US006420362B1

(12) United States Patent
Krüger et al.

(10) Patent No.: US 6,420,362 B1
(45) Date of Patent: Jul. 16, 2002

(54) AZINES CONTAINING THE 5,6-DI-HYDRO-(1,4,2) DIOXAZINE-3-YL GROUP AND THE USE THEREOF AS FUNGICIDES

(75) Inventors: Bernd-Wieland Krüger, Gladbach; Herbert Gayer, Monheim; Klaus Stenzel, Düsseldorf; Gerd Hänssler, Leverkusen; Astrid Mauler-Machnik, Leichlingen; Stefan Hillebrand, Neuss, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/529,203

(22) PCT Filed: Oct. 1, 1998

(86) PCT No.: PCT/EP98/06232

§ 371 (c)(1),
(2), (4) Date: Apr. 6, 2000

(87) PCT Pub. No.: WO99/19311

PCT Pub. Date: Apr. 22, 1999

(30) Foreign Application Priority Data

Oct. 14, 1997 (DE) .......................... 197 45 375
Feb. 12, 1998 (DE) .......................... 198 05 611

(51) Int. Cl.$^7$ .................. C07D 273/02; A61K 31/539; A01N 43/32
(52) U.S. Cl. ............. 514/229.2; 544/65; 564/250; 564/251
(58) Field of Search .............. 544/65; 514/229.2

(56) References Cited

FOREIGN PATENT DOCUMENTS

| EP | A-0 627 411 | * | 12/1994 |
| WO | WO-A-95 / 04728 | * | 2/1995 |
| WO | WO-A-97 / 00866 | * | 1/1997 |
| WO | WO-A-97 / 18187 | * | 5/1997 |
| WO | WO-A-98 / 17653 | * | 4/1998 |

OTHER PUBLICATIONS

Barton et al. Tetrahedron 44(1), 147–162 (1988).*
Chem. Ber. 40 (month unavailable) 1907, pp. 1622–1633, Otto Diels et al "Über die Kondensation von Oxalester mit Dimethylketol".
Chem. Ber. 38, (month unavailable) 1905 pp. 1917–1921, Otto Diels et al "Uber die Verwendbarkeit der Oximäther für Condensationen".
J. Chem. Soc. Perkin Trans. 2 (month unavailable) 1991, pp. 1809–1818, G. W. Adams et al, "The Complex Anionic Rearrangements of Deprotonated α–Oximino Carbonyl Derivatives in the Gas Phase".

* cited by examiner

Primary Examiner—Richard L Raymond
Assistant Examiner—Kahsay Habte
(74) Attorney, Agent, or Firm—Joseph C. Gil; Raymond J. Harmuth

(57) ABSTRACT

The present invention is directed to compounds of having the formula (I)

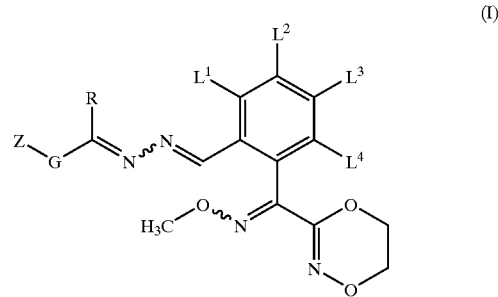

in which

G represents a single bond or a grouping

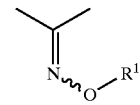

and

Z represents alkyl or halogenoalkyl or cycloalkyl or cycloalkylalkyl or heterocyclyl or heterocyclylalkyl or aryl or arylalkyl and $L^1$, $L^2$, $L^3$ and $L^4$ are identical or different and independently of one another in each case represent hydrogen, halogen, cyano, nitro or in each case optionally halogen-substituted alkyl, alkoxy, alkylthio, alkylsulphinyl or alkylsulphonyl having in each case 1 to 6 carbon atoms and in each case optionally substituted by 1 to 5 halogen atoms. The invention also relates to the preparation of such compounds and the use of such compounds to combat plant fungi and plant bacteria.

14 Claims, No Drawings

AZINES CONTAINING THE 5,6-DI-HYDRO-(1,4,2) DIOXAZINE-3-YL GROUP AND THE USE THEREOF AS FUNGICIDES

The invention relates to new azines, a process for their preparation and their use as fungicides.

It has already been disclosed that certain compounds which are structurally similar to those described below have fungicidal properties (compare, for example, WO 95-04728, WO 97-00866). However, the fungicidal action of these compounds leaves something to be desired, especially when low amounts are applied.

The new azines of the general formula (I)

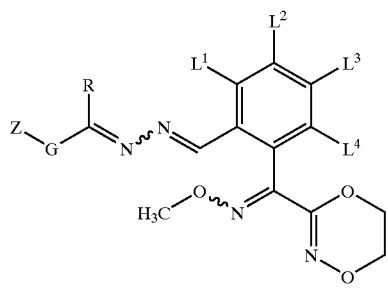

in which
G represents a single bond or a grouping

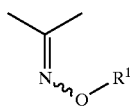

wherein
$R^1$ represents in each case optionally substituted alkyl, alkenyl, alkinyl or cycloalkyl,
R represents alkyl or optionally substituted cycloalkyl having 3 to 5 carbon atoms,
Z represents in each case optionally substituted alkyl, cycloalkyl, aryl, arylalkyl, heterocyclyl or heterocyclylalkyl and
$L^1$, $L^2$, $L^3$ and $L^4$ are identical or different and independently of one another in each case represent hydrogen, halogen, cyano, nitro or in each case optionally halogen-substituted alkyl, alkoxy, alkylthio, alkylsulphinyl or alkylsulphonyl,
have now been found.

In the definitions, the saturated or unsaturated hydrocarbon chains, such as alkyl, also when linked with heteroatoms, such as in alkoxy or alkylthio, are in each case straight-chain or branched.

Halogenoalkyl represents partly or completely halogenated alkyl. In the case of polyhalogenated halogenoalkyl, the halogen atoms can be identical or different. Preferred halogen atoms are fluorine and chlorine, and in particular fluorine. If the halogenoalkyl also carries further substituents, the maximum possible number of halogen atoms is reduced to the free valencies remaining.

Halogen in general represents fluorine, chlorine, bromine or iodine, preferably fluorine, chlorine or bromine, in particular fluorine or chlorine.

Heterocyclyl represents saturated or unsaturated and aromatic, cyclic compounds in which at least one ring member is a heteroatom, that is to say an atom other than carbon. If the ring contains several heteroatoms, these can be identical or different. Heteroatoms are preferably oxygen, nitrogen or sulphur. If the ring contains several oxygen atoms, these are not adjacent. If appropriate, the cyclic compounds form a polycyclic ring system together with further carbocyclic or heterocyclic, fuzed-on or bridged rings. Mono- or bicyclic ring systems are preferred, in particular mono- or bicyclic aromatic ring systems.

It has furthermore been found that the new azines of the general formula (I) are obtained by a process in which a) ketones of the general formula (II)

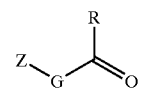

in which
G, R and Z have the abovementioned meanings, are reacted with an aldehyde of the general formula (III)

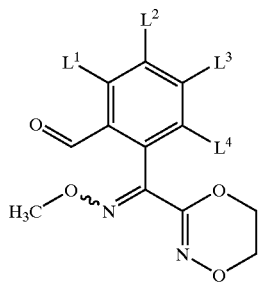

in which $L^1$, $L^2$, $L^3$ and $L^4$ have the abovementioned meanings, and hydrazine or hydrazine hydrate, optionally in the presence of a diluent and optionally in the presence of a catalyst, or by a process in which b) hydrazones of the formula (IV)

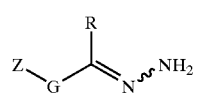

in which
G, R and Z have the abovementioned meanings, are reacted with an aldehyde of the general formula (III), optionally in the presence of a diluent and optionally in the presence of a catalyst, or by a process in which c) hydrazine derivatives of the formula (V)

$$\text{(V)}$$

in which
L¹, L², L³ and L⁴ have the abovementioned meanings,
are reacted with a ketone of the general formula (II), optionally in the presence of a diluent and optionally in the presence of a catalyst.

Finally, it has been found that the new azines of the general formula (I) show a very potent fungicidal action.

Where appropriate, the compounds according to the invention can be in the form of mixtures of various possible isomeric forms, in particular of stereoisomers, such as, for example, E and Z isomers or optical isomers. Both the E and the Z isomers, the individual enantiomers, the racemates and also any desired mixtures of these isomers are claimed.

Preferred azines of the formula (I) are those in which

G represents a single bond,

R represents alkyl having 1 to 4 carbon atoms, or cycloalkyl which has 3 to 6 carbon atoms and is optionally mono- to tetrasubstituted by halogen or alkyl, Z
represents cycloalkyl or cycloalkylalkyl which has in each case 3 to 7 carbon atoms in the cycloalkyl part and 1 to 4 carbon atoms in the alkyl part and is in each case optionally monosubstituted to tetrasubstituted by halogen or alkyl;
represents heterocyclyl or heterocyclylalkyl which has in each case 3 to 7 ring members and 1 to 4 carbon atoms in the alkyl part and is optionally substituted by halogen or alkyl having 1 to 4 carbon atoms;
or represents aryl or arylalkyl which has in each case 6 to 10 carbon atoms in the aryl part and 1 to 4 carbon atoms in the alkyl part and is in each case optionally monosubstituted to tetrasubstituted in the aryl part in an identical or different manner, the possible substituents preferably being chosen from the following list:
halogen, cyano, nitro, amino, formyl, carbamoyl, thiocarbamoyl;
in each case straight-chain or branched alkyl, alkoxy, alkoxyalkyl, alkylthioalkyl, alkylaminoalkyl, dialkylaminoalkyl, alkylthio, alkylsulphinyl or alkylsulphonyl having in each case 1 to 8 carbon atoms;
in each case straight-chain or branched alkenyl or alkenyloxy having in each case 2 to 6 carbon atoms;
in each case straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms;
in each case straight-chain or branched halogenoalkenyl or halogenoalkenyloxy having in each case 2 to 6 carbon atoms and 1 to 11 identical or different halogen atoms;
in each case straight-chain or branched alkylamino, dialkylamino, alkylcarbonyl, alkoxycarbonyl, alkylaminocarbonyl, dialkylaminocarbonyl, arylalkylaminocarbonyl, alkenylcarbonyl or alkinylcarbonyl having 1 to 6 carbon atoms in the particular hydrocarbon chains;
cycloalkyl or cycloalkyloxy having in each case 3 to 6 carbon atoms; in each case divalent alkylene having 3 or 4 carbon atoms, oxyalkylene having 2 or 3 carbon atoms or dioxyalkylene having 1 or 2 carbon atoms, in each case optionally monosubstituted to tetrasubstituted in an identical or different manner by fluorine, chlorine, oxo, methyl, trifluoromethyl or ethyl;
or a grouping wherein
A¹ represents hydrogen or alkyl having 1 to 4 carbon atoms or cycloalkyl having 3 to 6 carbon atoms and
A² represents hydroxyl, amino, methylamino, methyl, phenyl, benzyl, alkoxy, alkylamino or dialkylamino having 1 to 4 carbon atoms in the particular alkyl chains and
L¹, L², L³ and L⁴ are identical or different and independently of one another in each case represent hydrogen, halogen, cyano, nitro or alkyl, alkoxy, alkylthio, alkylsulphinyl or alkylsulphonyl having in each case 1 to 6 carbon atoms and in each case optionally substituted by 1 to 5 halogen atoms, preferably hydrogen or methyl, and in particular hydrogen.

Azines of the formula (I) which are likewise preferred are those in which

G represents a grouping wherein
R¹ represents hydrogen, or represents alkyl having 1 to 6 carbon atoms, alkenyl having 2 to 6 carbon atoms or alkinyl having 2 to 6 carbon atoms, in each case optionally substituted by halogen or alkoxy having 1 to 4 carbon atoms, or represents cycloalkyl which has 3 to 8 carbon atoms and is optionally substituted by halogen, alkyl or alkoxy having in each case 1 to 4 carbon atoms, or represents arylalkyl which has 1 to 4 carbon atoms in the alkyl part and is optionally substituted in the aryl part, the substituents being chosen from the following list:
halogen, cyano, nitro, formyl, carbamoyl, thiocarbamoyl, in each case straight-chain or branched alkyl, alkoxy, alkylthio, alkylsulphinyl or alkylsulphonyl having in each case 1 to 6 carbon atoms, in each case straight-chain or branched alkenyl, alkenyloxy or alkinyloxy having in each case 2 to 6 carbon atoms, in each case straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms, in each case straight-chain or branched halogenoalkenyl or halogenoalkenyloxy having in each case 2 to 6 carbon atoms and 1 to 11 identical or different halogen atoms, in each case straight-chain or branched alkylamino, dialkylamino, alkylcarbonyl, alkylcarbonyloxy, alkoxycarbonyl, alkylsulphonyloxy, hydroximinoalkyl or alkoximinoalkyl having in each case 1 to 6 carbon atoms in the individual alkyl parts, in each case divalent alkylene or dioxyalkylene which has in each case 1 to 6 carbon atoms and is in each case optionally monosubstituted or polysubstituted in an identical or different manner by halogen and/or straight-chain or branched alkyl having 1 to 4 carbon atoms and/or straight-chain or branched halogenoalkyl having 1 to 4 carbon atoms and 1 to 9 identical or different halogen atoms, R represents alkyl having 1 to 4 carbon atoms, or cycloalkyl which has 3 to 6 carbon atoms and is optionally monosubstituted to tetrasubstituted by halogen or alkyl, Z
represents alkyl or halogenoalkyl which has in each case 1 to 4 carbon atoms and is in each case optionally monosubstituted by cyano or alkoxy,
represents cycloalkyl or cycloalkylalkyl which has in each case 3 to 7 carbon atoms in the cycloalkyl part and 1 to 4 carbon atoms in the alkyl part and is in each case optionally monosubstituted to tetrasubstituted by halogen or alkyl;
represents heterocyclyl or heterocyclylalkyl which has in each case 3 to 7 ring members and 1 to 4 carbon atoms in the alkyl part and is optionally substituted by halogen or alkyl having 1 to 4 carbon atoms;
or represents aryl or arylalkyl which has in each case 6 to 10 carbon atoms in the aryl part and 1 to 4 carbon atoms in the alkyl part and is in each case optionally monosubstituted to tetrasubstituted in an identical or different manner in the aryl part, the possible substituents preferably being chosen from the following list:
halogen, cyano, nitro, amino, formyl, carbamoyl, thiocarbamoyl;
in each case straight-chain or branched alkyl, alkoxy, alkoxyalkyl, alkylthioalkyl, alkylaminoalkyl, dialkylaminoalkyl, alkylthio, alkylsulphinyl or alkylsulphonyl having in each case 1 to 8 carbon atoms;
in each case straight-chain or branched alkenyl or alkenyloxy having in each case 2 to 6 carbon atoms;
in each case straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms;
in each case straight-chain or branched halogenoalkenyl or halogenoalkenyloxy having in each case 2 to 6 carbon atoms and 1 to 11 identical or different halogen atoms;
in each case straight-chain or branched alkylamino, dialkylamino, alkylcarbonyl, alkoxycarbonyl, alkylaminocarbonyl, dialkylaminocarbonyl, arylalkylaminocarbonyl, alkenylcarbonyl or alkinylcarbonyl having 1 to 6 carbon atoms in the particular hydrocarbon chains;
cycloalkyl or cycloalkyloxy having in each case 3 to 6 carbon atoms; in each case divalent alkylene having 3 or 4 carbon atoms, oxyalkylene having 2 or 3 carbon atoms or dioxyalkylene having 1 or 2 carbon atoms, in each case optionally monosubstituted to tetrasubstituted in an identical or different manner by fluorine, chlorine, oxo, methyl, trifluoromethyl or ethyl;
or a grouping

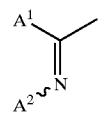

wherein
$A^1$ represents hydrogen or alkyl having 1 to 4 carbon atoms or cycloalkyl having 3 to 6 carbon atoms and
$A^2$ represents hydroxyl, amino, methylamino, methyl, phenyl, benzyl, alkoxy, alkylamino or dialkylamino having 1 to 4 carbon atoms in the particular alkyl chains and $L^1$, $L^2$, $L^3$ and $L^4$ are identical or different and independently of one another in each case represent hydrogen, halogen, cyano, nitro or alkyl, alkoxy, alkylthio, alkylsulphinyl or alkylsulphonyl having in each case 1 to 6 carbon atoms and in each case optionally substituted by 1 to 5 halogen atoms, preferably hydrogen or methyl, and in particular hydrogen.

Particularly preferred azines of the formula (I) are those in which
R represents methyl, ethyl, n- or i-propyl, or represents cyclopropyl, cyclobutyl or cyclopentyl, in each case optionally monosubstituted to tetrasubstituted by fluorine, chlorine, methyl or ethyl, in particular represents methyl.

Azines of the formula (I) which are also particularly preferred are those in which
G represents a single bond and
Z
represents cyclopentyl or cyclohexyl, in each case optionally monosubstituted to tetrasubstituted by fluorine, chlorine, methyl or ethyl;
represents thienyl, pyridyl, furyl, thienylmethyl, pyridylmethyl, benzopyrazolyl or furylmethyl, optionally substituted by methyl, ethyl, fluorine, chlorine or bromine;
or represents benzyl, 1-phenylethyl or 2-phenylethyl, in each case optionally monosubstituted to tetrasubstituted in an identical or different manner, in particular substituted phenyl, the possible substituents preferably being chosen from the following list:
fluorine, chlorine, bromine, cyano, nitro, amino, formyl, carbamoyl, thiocarbamoyl, methyl, ethyl, n- or i-propyl, n-, i-, s- or t-butyl, methoxymethyl, methoxy, ethoxy, n- or i-propoxy, methylthio, ethylthio, n- or i-propylthio, methylsulphinyl, ethylsulphinyl, methylsulphonyl or ethylsulphonyl, methylaminomethyl, dimethylaminomethyl, vinyl, allyl, 2-methylallyl, propen-1-yl, crotonyl, propargyl, vinyloxy, allyloxy, 2-methylallyloxy, propen-1-yloxy, crotonyloxy, propargyloxy;

trifluoromethyl, trifluoroethyl, difluoromethoxy, trifluoromethoxy, difluorochloromethoxy, trifluoroethoxy, pentafluoroethoxy, 2-chloro-1,1, 2-trifluoroethoxy, difluoromethylthio, trifluoromethylthio, difluorochloromethylthio, trifluoromethylsulphinyl or trifluoromethylsulphonyl, methylamino, ethylamino, n- or i-propylamino, dimethylamino, diethylamino, acetyl, propionyl, methoxycarbonyl, ethoxycarbonyl, methylaminocarbonyl, ethylaminocarbonyl, dimethylaminocarbonyl, diethylaminocarbonyl, acryloyl, propioloyl, cyclopentyl, cyclohexyl, or in each case divalent propanediyl, ethyleneoxy, methylenedioxy or ethylenedioxy, in each case optionally monosubstituted to tetrasubstituted in an identical or different manner by fluorine, chlorine, oxo, methyl or trifluoromethyl, or a grouping

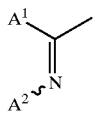

wherein
A¹ represents hydrogen or methyl and
A² represents hydroxyl, methoxy, ethoxy, amino, methylamino, methyl, phenyl or benzyl.

Azines of the formula (I) which are furthermore particularly preferred are those in which
G represents the grouping

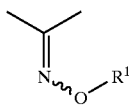

wherein
R¹ represents hydrogen, methyl, ethyl, n- or i-propyl, n-, i-, s- or t-butyl, allyl, propargyl or but-2-en-1-yl and Z
represents methyl, ethyl, n- or i-propyl, n-, i-, s- or t-butyl or trifluoromethyl, or represents cyclopentyl or cyclohexyl, in each case optionally monosubstituted to tetrasubstituted by fluorine, chlorine, methyl or ethyl;
represents thienyl, pyridyl, furyl, thienylmethyl, pyridylmethyl or furylmethyl, optionally substituted by methyl, ethyl, fluorine, chlorine or bromine;
or represents benzyl, 1-phenylethyl or 2-phenylethyl, in each case optionally monosubstituted to tetrasubstituted in an identical or different manner, in particular substituted phenyl, the possible substituents preferably being chosen from the following list:
fluorine, chlorine, bromine, cyano, nitro, amino, formyl, carbamoyl, thiocarbmoyl, methyl, ethyl, n- or i-propyl, n-, i-, s- or t-butyl, methoxymethyl, methoxy, ethoxy, n- or i-propoxy, methylthio, ethylthio, n- or i-propylthio, methylsulphinyl, ethylsulphinyl, methylsulphonyl or ethylsulphonyl, methylaminomethyl, dimethylaminomethyl, vinyl, allyl, 2-methylallyl, propen-1-yl, crotonyl, propargyl, vinyloxy, allyloxy, 2-methylallyloxy, propen-1-yloxy, crotonyloxy, propargyloxy;

trifluoromethyl, trifluoroethyl, difluoromethoxy, trifluoromethoxy, difluorochloromethoxy, trifluoroethoxy, pentafluoroethoxy, 2-chloro-1,1, 2-trifluoroethoxy, difluoromethylthio, trifluoromethylthio, difluorochloromethylthio, trifluoromethylsulphinyl or trifluoromethylsulphonyl, methylamino, ethylamino, n- or i-propylamino, dimethylamino, diethylamino, acetyl, propionyl, methoxycarbonyl, ethoxycarbonyl, methylaminocarbonyl, ethylaminocarbonyl, dimethylaminocarbonyl, diethylaminocarbonyl, acryloyl, propioloyl, cyclopentyl, cyclohexyl, or in each case divalent propanediyl, ethyleneoxy, methylenedioxy or ethylenedioxy, in each case optionally monosubstituted to tetrasubstituted in an identical or different manner by fluorine, chlorine, oxo, methyl or trifluoromethyl, or a grouping

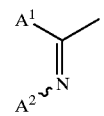

wherein
A¹ represents hydrogen or methyl and
A² represents hydroxyl, methoxy, ethoxy, amino, methylamino, methyl, phenyl or benzyl.

Azines of the formula (I) which are also particularly preferred are those in which
L¹, L², L³ and L⁴ are identical or different and independently of one another in each case represent hydrogen, fluorine, chlorine, bromine, cyano, nitro, methyl, ethyl, n- or i-propyl, n-, i-, s- or t-butyl, methoxy, ethoxy, n- or i-propoxy, methylthio, ethylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, preferably hydrogen or methyl, and in particular hydrogen.

The definitions of radicals listed above generally or stated in the preferred ranges apply both to the end products of the formula (I) and correspondingly to the particular starting substances or intermediate products required for the preparation.

These definitions of radicals can be combined with one another as desired, that is to say also between the stated ranges of preferred compounds.

Formula (II) provides a general definition of the ketones required as starting substances for carrying out process a) according to the invention. In this formula (II), G, R and Z preferably or in particular have those meanings which have already been mentioned as preferred or as particularly preferred for G, R and Z in connection with the description of the compounds of the formula (I) according to the invention.

The ketones of the formula (II) are known synthesis chemicals or can be prepared by customary standard methods.

Formula (III) provides a general definition of the aldehydes furthermore required as starting substances for carrying out process a) according to the invention. In this formula (III), $L^1$, $L^2$, $L^3$ and $L^4$ preferably or in particular have those meanings which have already been mentioned as preferred or as particularly preferred for $L^1$, $L^2$, $L^3$ and $L^4$ in connection with the description of the compounds of the formula (I) according to the invention.

The aldehydes of the formula (III) are obtained by a process in which, for example, halogenomethyl compounds of the general formula (VI)

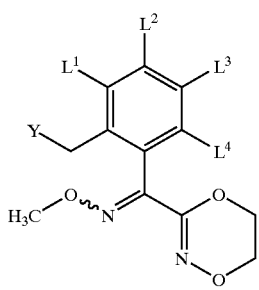

(VI)

in which $L^1$, $L^2$, $L^3$ and $L^4$ have the abovementioned meanings and

Y represents halogen, are reacted, for example, with an amine oxide, optionally in the presence of a diluent.

The halogenomethyl compounds of the formula (VI) required for the preparation of the aldehydes of the formula (III) are obtained, for example, by a process in which phenoxy compounds of the general formula (VII)

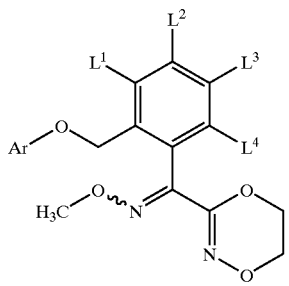

(VII)

in which $L^1$, $L^2$, $L^3$ and $L^4$ have the abovementioned meanings and

Ar represents optionally substituted phenyl are reacted with a carboxylic acid halide, such as, for example, acetylchloride, optionally in the presence of a diluent, such as, for example, methylene chloride, and optionally in the presence of a Lewis acid, such as, for example, aluminium chloride.

The phenoxy compounds of the formula (VII) are known and/or can be prepared by known methods (compare, for example, WO-A 95 04 728 and DE-A 195 04 625).

Formula (IV) provides a general definition of the hydrazones required as starting substances for carrying out process b) according to the invention. In this formula (IV), G, R and Z preferably or in particular have those meanings which have already been mentioned as preferred or as particularly preferred for G, R and Z in connection with the description of the compounds of the formula (I) according to the invention.

The hydrazones of the formula (IV) are known or can be prepared from the ketones of the formula (II) described above and hydrazine by customary standard methods.

The hydrazones of the formula (IV-a)

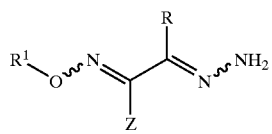

in which

R, $R^1$ and Z have the abovementioned meanings are new and the present invention also relates to them.

They are obtained (process d) by a process in which ketones of the formula (II-a)

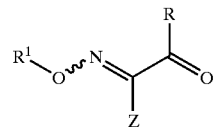

in which

R, $R^1$ and Z have the abovementioned meanings, are reacted with hydrazine, hydrazine hydrate or one of its salts, optionally in the presence of a diluent and optionally in the presence of a catalyst.

Formula (II-a) provides a general definition of the ketones required as starting substances for carrying out process d) according to the invention. In this formula (II-a), R, $R^1$ and Z preferably or in particular have those meanings which have already been mentioned as preferred or as particularly preferred for R, $R^1$ and Z in connection with the description of the compounds of the formula (1) according to the invention.

The ketones of the formula (II-a) are known (Chem Ber. 40, 1907, 1624; Chem Ber. 38, 1905, 1919; J. Chem. Soc. 11, 1991, 1809–1818) or can be prepared by known methods.

The hydrazine or hydrazine hydrate or its salts furthermore required as a starting substance for carrying out process d) according to the invention are known synthesis chemicals.

The aldehydes of the formula (III) furthermore required as starting substances for carrying out process b) according to the invention have already been described above in the description of process a) according to the invention.

Formula (V) provides a general definition of the hydrazine derivatives required as starting substances for carrying out process c) according to the invention. In this formula (V), $L^1$, $L^2$, $L^3$ and $L^4$ preferably or in particular have those meanings which have already been mentioned as preferred or as particularly preferred for $L^1$, $L^2$, $L^3$ and $L^4$ in connection with the description of the compounds of the formula (I) according to the invention.

The hydrazine derivatives of the formula (V) are not yet known, and the present application also relates to them as new compounds. They are obtained (process e)) by a process in which aldehydes of the formula (III) are reacted with hydrazine, hydrazine hydrate or one of its salts, optionally in the presence of a diluent and optionally in the presence of a catalyst.

The ketones of the formula (II) furthermore required as starting substances for carrying out process c) according to the invention have already been described above in the description of process a) according to the invention.

Possible diluents for carrying out processes a), b), c), d) and e) according to the invention are all the inert organic solvents. These include, preferably, aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, methylene chloride, chloroform, carbon tetrachloride, dichloroethane or trichloroethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisole; sulphoxides, such as dimethylsulphoxide; sulphones, such as sulpholane; or alcohols, such as methanol, ethanol, n- or i-propanol, n-, i-, sec- or tert-butanol, ethanediol, propane-1,2-diol, ethoxyethanol, methoxyethanol, diethylene glycol monomethyl ether or diethylene glycol monoethyl ether.

Processes a), b), c), d) and e) according to the invention are optionally carried out in the presence of a catalyst. Possible catalysts are inorganic and organic acids. These include, for example, sulphuric acid, phosphoric acid, formic acid, trifluoroacetic acid, methanesulphonic acid, trifluoromethanesulphfonic acid, toluenesulphonic acid, acid ion exchangers, acid aluminas and acid silica gel.

The reaction temperatures can be varied within a substantial range in carrying out processes a), b), c), d) and e) according to the invention. In general, the reaction is carried out at temperatures from 20° C. to 180° C., preferably at temperatures from 20° C. to 150° C.

For carrying out process a) according to the invention for the preparation of the compounds of the formula (I), in general 0.5 to 2 mol, preferably 0.8 to 1.5 mol, of aldehyde of the formula (III) and 0.5 to 2 mol, preferably 0.8 to 1.5 mol, of hydrazine or hydrazine hydrate are employed per mole of ketone of the formula (II).

For carrying out process b) according to the invention for the preparation of the compounds of the formula (I), in general 0.5 to 2 mol, preferably 0.8 to 1.5 mol, of aldehyde of the formula (III) are employed per mole of hydrazone of the formula (IV).

For carrying out process c) according to the invention for the preparation of the compounds of the formula (I), in general 0.5 to 2 mol, preferably 0.8 to 1.5 mol, of hydrazine derivative of the formula (V) are employed per mole of ketone of the formula (II).

Processes a), b), c), d) and e) according to the invention are in general carried out under normal pressure. However, it is also possible to carry out the processes under increased or reduced pressure—in general under between 0.1 bar and 10 bar.

The reaction is carried out and the reaction products are worked up and isolated by generally customary processes (compare also the preparation examples).

The substances according to the invention have a potent microbicidal action and can be employed for combating undesirable microorganisms, such as fungi and bacteria, in plant protection and the preservation of materials.

Fungicides can be employed in plant protection for combating Plasmodiophoromycetes, Oomycetes, Chytridiomycetes, Zygomycetes, Ascomycetes, Basidiomycetes and Deuteromycetes.

Bactericides can be employed in plant protection for combating Pseudomonadaceae, Rhizobiaceae, Enterobacteriaceae, Corynebacteriaceae and Streptomycetaceae.

Some causative organisms of fungal and bacterial diseases which come under the generic names listed above and which may be mentioned as examples, but not by way of limitation, are:

Xanthomonas species, such as, for example, *Xanthomonas campestris* pv. *oryzae;*

Pseudomonas species, such as, for example, *Pseudomonas syringae* pv. *lachrymans;*

Erwinia species, such as, for example, *Erwinia amylovora;*

Pythium species, such as, for example, *Pythium ultimum;*

Phytophthora species, such as, for example, *Phytophthora infestans;*

Pseudoperonospora species, such as, for example, *Pseudoperonospora humuli* or *Pseudoperonospora cubensis;*

Plasmopara species, such as, for example, *Plasmopara viticola;*

Bremia species, such as, for example, *Bremia lactucae;*

Peronospora species, such as, for example, *Peronospora pisi* or *P. brassicae;*

Erysiphe species, such as, for example, *Erysiphe graminis;*

Sphaerotheca species, such as, for example, *Sphaerotheca fuliginea;*

Podosphaera species, such as, for example, *Podosphaera leucotricha;*

Venturia species, such as, for example, *Venturia inaequalis;*

Pyrenophora species, such as, for example, *Pyrenophora teres* or *P. graminea* (conidia form: Drechslera, syn: Helminthosporium);

Cochliobolus species, such as, for example, *Cochliobolus sativus* (conidia form: Drechslera, syn: Helminthosporium);

Uromyces species, such as, for example, *Uromyces appendiculatus;*

Puccinia species, such as, for example, *Puccinia recondita;*

Sclerotinia species, such as, for example, *Sclerotinia sclerotiorum;*

Tilletia species, such as, for example, *Tilletia caries;*

Ustilago species, such as, for example, *Ustilago nuda* or *Ustilago avenae;*

Pellicularia species, such as, for example, *Pellicularia sasakii;*

Pyricularia species, such as, for example, *Pyricularia oryzae;*

Fusarium species, such as, for example, *Fusarium culmorum;*

Botrytis species, such as, for example, *Botrytis cinerea;*

Septoria species, such as, for example, *Septoria nodorum;*

Leptosphaeria species, such as, for example, *Leptosphaeria nodorum;*

Cercospora species, such as, for example, *Cercospora canescens;*

Alternaria species, such as, for example, *Alternaria brassicae;*

Pseudocercosporella species, such as, for example, *Pseudocercosporella herpotrichoides.*

The good toleration by plants of the active compounds in the concentrations necessary for combating plant diseases allows treatment of above-ground parts of plants, of vegetative propagation stock and seeds, and of the soil.

The active compounds according to the invention can be used here with particularly good success for combating cereal diseases, such as, for example, against Leptosphaeria, Fusarium or Puccinia species, diseases in wine-, fruit- and vegetable-growing, such as, for example, against Phytophtora or Plasmopara species, or rice diseases, such as, for example, against Pyricularia species.

The active compounds according to the invention are also suitable for increasing the harvest yield. They are moreover of low toxicity and have a good tolerance by plants.

The active compounds can be converted into the customary formulations, depending on their particular physical and/or chemical properties, such as solutions, emulsions, suspensions, powders, foams, pastes, granules, aerosols, microencapsulations in polymeric substances and in coating compositions for seed, as well as ULV cold mist and warm mist formulations.

These formulations are prepared in a known manner, for example by mixing the active compounds with extenders, that is to say liquid solvents, liquefied gases under pressure and/or solid carriers, optionally using surface-active agents, that is to say emulsifiers and/or dispersing agents and/or foam-forming agents. In the case of the use of water as an extender, organic solvents can also be used, for example, as auxiliary solvents. Possible liquid solvents are essentially: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol and ethers and esters thereof, ketones, such as acetone, methyl ethyl ketone, methyl isobutyl ketone or cyclohexanone, strongly polar solvents, such as dimethylformamide and dimethylsulphoxide, and water. Liquefied gaseous extenders or carriers are understood as meaning those liquids which are gaseous at normal temperature and under normal pressure, for example aerosol propellent gases, such as halogenohydrocarbons and butane, propane, nitrogen and carbon dioxide. Possible solid carriers are: for example, naturally occurring rock powders, such as kaolins, aluminas, talc, chalk, quartz, attapulgite, montmorillonite or diatomaceous earth, and synthetic rock powders, such as highly disperse silicic acid, aluminium oxide and silicates. Possible solid carriers for granules are: for example, crushed and fractionated natural rocks, such as calcite, marble, pumice, sepiolite and dolomite, and synthetic granules of inorganic and organic flours and granules of organic material, such as sawdust, coconut shells, maize cobs and tobacco stalks. Possible emulsifiers and/or foam-forming agents are: for example, nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates. Possible dispersing agents are: for example, lignin-sulphite waste liquors and methylcellulose.

Adhesives, such as carboxymethylcellulose, naturally occurring and synthetic pulverulent, granular or latex-like polymers, such as gum arabic, polyvinyl alcohol and polyvinyl acetate, and naturally occurring phospholipids, such as cephalins and lecithins, and synthetic phospholipids, can be used in the formulations. Other additives can be mineral and vegetable oils.

It is possible to use dyestuffs, such as inorganic pigments, for example iron oxide, titanium oxide and Prussian blue, and organic dyestuffs, such as alizarin, azo and metal phthalocyanine dyestuffs, and trace nutrients, such as salts of iron, manganese, boron, copper, cobalt, molybdenum and zinc.

The formulations in general comprise between 0.1 and 95 percent by weight of active compound, preferably between 0.5 and 90%.

The active compounds can be converted into the customary formulations, depending on their particular physical and/or chemical properties, such as solutions, emulsions, suspensions, powders, foams, pastes, granules, aerosols, microencapsulations in polymeric substances and in coating compositions for seed, as well as ULV cold and warm mist formulations.

The active compounds according to the invention can also be used, as such or in their formulations, as a mixture with known fungicides, bactericides, acaricides, nematicides or insecticides in order thus to broaden the action spectrum or to prevent development of resistance. In many cases, synergistic effects are obtained here, that is to say the activity of the mixture is greater than the activity of the individual components.

Possible mixing partners are, for example, the following compounds:

Fungicides:

aldimorph, ampropylfos, ampropylfos-potassium, andoprim, anilazine, azaconazole, azoxystrobin, benalaxyl, benodanil, benomyl, benzamacril, benzamacril-isobutyl, bialaphos, binapacryl, biphenyl, bitertanol, blasticidin-S, bromuconazole, bupirimat, buthiobat, calcium polysulphide, capsimycin, captafol, captan, carbendazim, carboxin, carvon, chinomethionat (quinomethionate), chlobenthiazon, chlorfenazole, chloroneb, chloropicrin, chlorothalonil, chlozolinat, clozylacon, cufraneb, cymoxanil, cyproconazole, cyprodinil, cyprofuram, debacarb, dichlorophen, diclobutrazol, diclofluanid, diclomezin, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon, ediphenphos, epoxiconazole, etaconazole, ethirimol, etridiazole, famoxadon, fenapanil, fenarimol, fenbuconazole, fenfuram, fenitropan, fenpiclonil, fenpropidin, fenpropimorph, fentin acetate, fentin hydroxide, ferbam, ferimizon, fluazinam, flumetover, fluoromid, fluquinconazole, flurprimidol, flusilazol, flusulfamid, flutolanil, flutriafol, folpet, fosetyl-aluminium, fosetyl-sodium, fthalid, fuberidazole, furalaxyl, furametpyr, furcarbonil, furconazole, furconazole-cis, furmecyclox, guazatin, hexachlorobenzene, hexaconazole, hymexazole, imazalil, imibenconazole, iminoctadine, iminoctadine albesilate, iminoctadine triacetate, iodocarb, ipconazole, iprobenfos (IBP), iprodione, irumamycin, isoprothiolan, isovaledione, kasugamycin, kresoxim-methyl, copper formulations, such as: copper hydroxide, copper naphthenate, copper oxychloride, copper sulphate, copper oxide, oxine-copper and Bordeaux mixture, mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin, nickel dimethyldithiocarbamate, nitrothal-isopropyl, nuarimol, ofurace, oxadixyl, oxamocarb, oxolinic acid, oxycarboxime, oxyfenthiin, paclobutrazole, pefurazoate, penconazole, pencycuron, phosdiphen, pimaricin, piperalin, polyoxin, polyoxorim, probenazole, prochloraz, procymidon, propamocarb, propanosine-sodium, propiconazole, propineb, pyrazophos, pyrifenox, pyrimethanil, pyroquilon, pyroxyfur, quinconazole, quintozene (PCNB), sulphur and sulphur formulations, tebuconazole, tecloftalam, tecnazene, tetcyclacis, tetraconazole, thiabendazole, thicyofen, thifluzamide, thiophanate-methyl, thiram, tioxymid, tolclofos-methyl, tolylfluanid, triadimefon, triadimenol, triazbutil, triazoxid, trichlamid, tricyclazole, tridemorph, triflumizol, triforin, triticonazole, uniconazole, validamycin A, vinclozolin, viniconazole, zarilamid, zineb, ziram and Dagger G,

OK-8705,

OK-8801,

α-(1,1-dimethylethyl)-β-(2-phenoxyethyl)-1H-1,2,4-triazole-1-ethanol,

α-(2,4-dichlorophenyl)-β-fluoro-β-propyl-1H-1,2,4-triazole-1-ethanol,

α-(2,4-dichlorophenyl)-β-methoxy-α-methyl-1H-1,2,4-triazole-1-ethanol,

α-(5-methyl-1,3-dioxan-5-yl)-β-[[4-(trifluoromethyl)-phenyl]-methylene]-1H-1,2,4-triazole-1-ethanol, (5RS,6RS)-6-hydroxy-2,2,7,7-tetramethyl-5-(1H-1,2,4-triazol-1-yl)-3-octanone, (E)-α-(methoxyimino)-N-methyl-2-phenoxy-phenylacetamide, {2-methyl-1-[[[1-(4-methylphenyl)-ethyl]-amino]-carbonyl]-propyl}-carbamic acid 1-isopropylester 1-(2,4-dichlorophenyl)-2-(1H-1,2,4-triazol-1-yl)-ethanone O-(phenylmethyl)-oxime, 1-(2-methyl-1-naphthalenyl)-1H-pyrrole-2,5-dione, 1-(3,5-dichlorophenyl)-3-(2-propenyl)-2,5-pyrrolidinedione, 1-[(diiodomethyl)-sulphonyl]-4-methyl-benzene, 1-[[2-(2,4-dichlorophenyl)-1,3-dioxolan-2-yl]-methyl]-1H-imidazole, 1-[[2-(4-chlorophenyl)-3-phenyloxiranyl]-methyl]-1H-1,2,4-triazole, 1-[1-[2-[(2,4-dichlorophenyl)-methoxy]-phenyl]-ethenyl]-1H-imidazole, 1-methyl-5-nonyl-2-(phenylmethyl)-3-pyrrolidinol, 2',6'-dibromo-2-methyl-4'-trifluoromethoxy-4'-trifluoromethyl-1,3-thiazole-5-carboxanilide, 2,2-dichloro-N-[1-(4-chlorophenyl)-ethyl]-1-ethyl-3-methyl-cyclopropanecarboxamide, 2,6-dichloro-5-(methylthio)-4-pyrimidinyl thiocyanate, 2,6-dichloro-N-(4-trifluoromethylbenzyl)-benzamide, 2,6-dichloro-N-[[4-(trifluoromethyl)-phenyl]-methyl]-benzamide, 2-(2,3,3-triiodo-2-propenyl)-2H-tetrazole, 2-[(1-methylethyl)-sulphonyl]-5-(trichloromethyl)-1,3,4-thiadiazole, 2-[[6-deoxy-4-O-(4-O-methyl-β-D-glycopyranosyl)-α-D-glucopyranosyl]-amino]-4-methoxy-1H-pyrrolo[2,3-d]pyrimidine-5-carbonitrile, 2-aminobutane, 2-bromo-2-(bromomethyl)-pentanedinitrile, 2-chloro-N-(2,3-dihydro-1,1,3-trimethyl-1H-inden-4-yl)-3-pyridinecarboxamide, 2-chloro-N-(2,6-dimethylphenyl)-N-(isothiocyanatomethyl)-acetamide, 2-phenylphenol(OPP), 3,4-dichloro-1-[4-(difluoromethoxy)-phenyl]-1H-pyrrole-2,5-dione, 3,5-dichloro-N-[cyano[(1-methyl-2-propynyl)-oxy]-methyl]-benzamide, 3-(1,1-dimethylpropyl-1-oxo-1H-indene-2-carbonitrile, 3-[2-(4-chlorophenyl)-5-ethoxy-3-isoxazolidinyl]-pyridine, 4-chloro-2-cyano-N,N-dimethyl-5-(4-methylphenyl)-1H-imidazole-1-sulphonamide, 4-methyl-tetrazolo[1,5-a]quinazolin-5(4H)-one, 8-(1,1-dimethylethyl)-N-ethyl-N-propyl-1,4-dioxaspiro[4.5]decane-2-methanamine, 8-hydroxyquinoline sulphate, 9H-xanthene-9-carboxylic acid 2-[(phenylamino)-carbonyl]-hydrazide, bis-(1-methylethyl)-3-methyl-4-[(3-methylbenzoyl)-oxy]-2,5-thiophenedicarboxylate, cis-1-(4-chlorophenyl)-2-(1H-1,2,4-triazol-1-yl)-cycloheptanol, cis-4-[3-[4-(1,1-dimethylpropyl)-phenyl-2-methylpropyl]-2,6-dimethyl-morpholine hydrochloride, ethyl [(4-chlorophenyl)-azo]-cyanoacetate, potassium bicarbonate, methanetetrathiol sodium salt, methyl 1-(2,3-dihydro-2,2-dimethyl-1H-inden-1-yl)-1H-imidazole-5-carboxylate, methyl N-(2,6-dimethylphenyl)-N-(5-isoxazolylcarbonyl)-DL-alaninate, methyl-N-(chloroacetyl)-N-(2,6-dimethylphenyl)-DL-alaninate, N-(2,3-dichloro-4-hydroxyphenyl)-1-methyl-cyclohexanecarboxamide, N-(2,6-dimethylphenyl)-2-methoxy-N-(tetrahydro-2-oxo-3-furanyl)-acetamide, N-(2,6-dimethylphenyl)-2-methoxy-N-(tetrahydro-2-oxo-3-thienyl)-acetamide, N-(2-chloro-4-nitrophenyl)-4-methyl-3-nitro-benzenesulphonamide, N-(4-cyclohexylphenyl)-1,4,5,6-tetrahydro-2-pyrimidinamine, N-(4-hexylphenyl)-1,4,5,6-tetrahydro-2-pyrimidinamine, N-(5-chloro-2-methylphenyl)-2-methoxy-N-(2-oxo-3-oxazolidinyl)-acetamide, N-(6-methoxy-3-pyridinyl)-cyclopropanecarboxamide, N-[2,2,2-trichloro-1-[(chloroacetyl)-amino]-ethyl]-benzamide, N-[3-chloro-4,5-bis-(2-propinyloxy)-phenyl]-N'-methoxy-methanimide-amide, N-formyl-N-hydroxy-DL-alanine sodium salt, O,O-diethyl [2-(dipropylamino)-2-oxoethyl]-ethylphosphoramidothioate, O-methyl S-phenyl phenylpropylphosphoramidothioate, S-methyl 1,2,3-benzothiadiazole-7-carbothioate, spiro[2H]-1-benzopyran-2,1'(3'H)-isobenzofuran-3'-one, Bactericides:
bronopol, dichlorophen, nitrapyrin, nickel-dimethyldithiocarbamate, kasugamycin, octhilinon, furancarboxylic acid, oxytetracycline, probenazole, streptomycin, tecloftalam, copper sulphate and other copper formulations.

Insecticides/acaricides/nematicides:
abamectin, acephate, acrinathrin, alanycarb, aldicarb, alphamethrin, amitraz, avermectin, AZ 60541, azadirachtin, azinphos A, azinphos M, azocyclotin,

*Bacillus thuringiensis*, 4-bromo-2-(4-chlorophenyl)-1-(ethoxymethyl)-5-(trifluoro-methyl)-1H-pyrrole-3- carbonitrile, bendiocarb, benfuracarb, bensultap, betacyfluthrin, bifenthrin, BPMC, brofenprox, bromophos A, bufencarb, buprofezin, butocarboxim, butylpyridaben, cadusafos, carbaryl, carbofuran, carbophenothion, carbosulfan, cartap, chloethocarb, chlorethoxyfos, chlorfenapyr, chlorfenvinphos, chlorfluazuron, chlormephos, N-[(6-chloro-3-pyridinyl)-methyl]-N'-cyano-N-methyl-ethanimideamide, chlorpyrifos, chlorpyrifos M, cis-resmethrin, clocythrin, clofentezin, cyanophos, cycloprothrin, cyfluthrin, cyhalothrin, cyhexatin, cypennethrin, cyromazin, deltamethrin, demeton M, demeton S, demeton-S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfen valerate, ethiofencarb, ethion, ethofenprox, ethoprophos, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, fluazuron, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivermectin, lamda-cyhalothrin, lufenuron, malathion, mecarbam, mevinphos, mesulfenphos, metaldehyde, methacrifos, methamidophos, methidathion, methiocarb, methomyl, metolcarb, milbemectin, monocrotophos, moxidectin, naled, NC 184, nitenpyram omethoate, oxamyl, oxydemethon M, oxydeprofos, parathion A, parathion M, permethrin, phenthoate, phorate, phosalone, phosmet, phosphamidon, phoxim, pirimicarb, pirimiphos M, pirimiphos A, profenophos, promecarb, propaphos, propoxur, prothiophos, prothoate, pymetrozin, pyrachlophos, pyridaphenthion, pyresmethrin, pyrethrum, pyridaben, pyrimidifen, pyriproxifen, quinalphos, salithion, sebufos, silafluofen, sulfotep, sulprofos, tebufenozide, tebufenpyrad, tebupirimiphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb, vamidothion, XMC, xylylcarb, zetamethrin.

A mixture with other known active compounds, such as herbicides, or with fertilizers and growth regulators, is also possible.

The active compounds can be used as such, in the form of their formulations or the use forms prepared therefrom, such as ready-to-use solutions, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seed of the plants can also be treated.

When the active compounds according to the invention are employed as fungicides, the amounts applied can be varied within a substantial range, depending on the method of application. In the treatment of parts of plants, the amounts of active compound applied are in general between 0.1 and 10,000 g/hectare, preferably between 10 and 1000 g/hectare. In the treatment of seed, the amounts of active compound applied are in general between 0.001 and 50 g per kilogram of seed, preferably between 0.01 and 10 g per kilogram of seed. In the treatment of soil, the amounts of active compound applied are in general between 0.1 and 10,000 g/ha, preferably between 1 and 5000 g/ha.

PREPARATION EXAMPLES

Example (1)

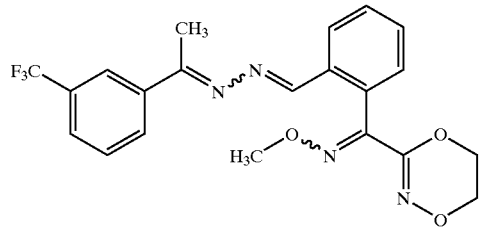

(Process a)

0.9 g (0.0036 mol) of 2-[(5,6-dihydro-[1,4,2]dioxazin-3-yl)-methoxyimino-methyl]-benzaldehyde, 0.69 g (0.0036 mol) of 3-trifluoromethylacetophenone, 0.18 g (0.0036 mol) of hydrazine hydrate and 25 mg of 4-toluenesulphonic acid are heated under reflux in 120 ml of toluene for 18 hours using a water separator. After cooling, the mixture is dried over magnesium sulphate and concentrated under reduced pressure. The residue is chromatographed over silica gel with cyclohexane/ethyl acetate (5:1). 0.45 g (29% of theory) of (5,6-dihydro-[1,4,2]dioxazin-3-yl)-(2-{[1-(3-trifluoromethylphenyl)-ethylidene]-hydrazonomethyl}-phenyl)-methanone O-methyl oxime is obtained.

HPLC: log P=3.80

The log P values were determined in accordance with EEC Directive 79/831 Annex V. A8 by HPLC (gradient method, acetonitrile/0.1% strength aqueous phosphoric acid).

Preparation of the Starting Substance

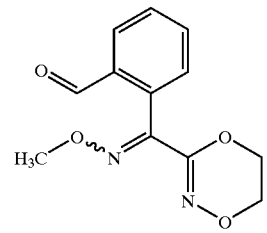

19.5 g (0.14 mol) of N-methylmorpholine N-oxide are added to a solution of 15 g (0.056 mol) of (2-chloromethyl-phenyl)-(5,6-dihydro-[1,4,2]dioxazin-3-yl)-methanone O-methyl oxime in 150 ml of dimethylformamide and the mixture is stirred at 120° C. for 2 hours. After cooling, the mixture is poured into 1000 ml of water and extracted three times with 200 ml of ethyl acetate each time. The combined organic phases are dried over magnesium sulphate and concentrated under reduced pressure. The residue is stirred with diisopropyl ether and the solid formed is filtered off with suction. 10.5 g (76% of theory) of 2-[(5,6-dihydro-[1,4,2]dioxazin-3-yl)-methoxyimino-methyl]-benzaldehyde are obtained.

¹H-NMR (CDCl₃, TMS): δ3.96; 4.17–4.20; 4.53–4.56; 7.29–7.95; 9.92 ppm.

Preparation of the Precursor

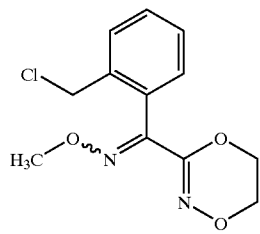

61.1 g (0.775 mmol) of acetyl chloride are added to a suspension of 103.4 g (0.775 mol) of anhydrous aluminium chloride in 1 l of methylene chloride in the course of 15 minutes. A solution of 105 g (0.31 mol) of (5,6-dihydro-[1,4,2]dioxazin-3-yl)-(2-o-tolyloxymethyl-phenyl)-methanone O-methyl oxime in 500 ml of methylene chloride is added dropwise to this mixture at 20° C. under argon, the reaction mixture heating up to 30° C., and the mixture is stirred for a further 3 hours. The reaction mixture is poured onto 2 l of ice-water and extracted 3 times with 300 ml of methylene chloride each time. The combined organic phases are dried over magnesium sulphate and concentrated under reduced pressure. The residue is stirred with diisopropyl ether and the solid formed is filtered off with suction (59.1 g). The filtrate is concentrated under reduced pressure and the residue is chromatographed over silica gel with cyclohexane/ethyl acetate (3:1). A further 4 g of product are obtained. 63.1 g (76% of theory) of (2-chloromethyl-phenyl)-(5,6-dihydro-[1,4,2]dioxazin-3-yl)-methanone O-methyl oxime are obtained in total.

¹H-NMR (CDCl₃, TMS): δ=3.99; 4.17–4.20; 4.49–4.53; 7.15–7.53 ppm.

Example (2)

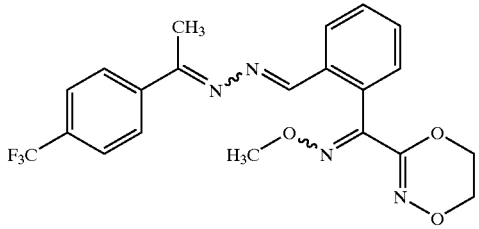

(Process b)

0.4 g (0.0016 mol) of 2-[(5,6-dihydro-[1,4,2]dioxazin-3-yl)-methoxyimino-methyl]-benzaldehyde and 0.325 g (0.0016 mol) of 4-trifluoromethylacetophenone hydrazone are heated under reflux in 10 ml of methanol for 18 hours. After cooling, the mixture is poured into 100 ml of water and extracted three times with 50 ml of ethyl acetate each time. The organic phase is separated off, washed with 50 ml of water, dried over magnesium sulphate and concentrated under reduced pressure. The residue is chromatographed over silica gel with cyclohexane/ethyl acetate (3:1). 0.50 g (72% of theory) of (5,6-dihydro-[1,4,2]dioxazin-3-yl)-(2-{[1-(4-trifluoromethylphenyl)-ethylidene]-hydrazonomethyl}-phenyl)-methanone O-methyl oxime is obtained.

HPLC: log P=3.80

Preparation of the Starting Substance

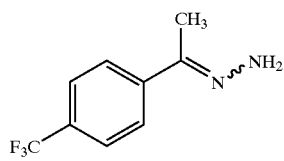

24.5 g (0.13 mol) of 4-trifluoromethylacetophenone and 26 g (0.52 mol) of hydrazine hydrate are heated under reflux in 100 ml of methanol for 1.5 hours. After cooling, the mixture is poured into 800 ml of water and extracted three times with 200 ml of methylene chloride each time. The organic phase is separated off, dried over magnesium sulphate and concentrated under reduced pressure. 23.5 g (89% of theory) of 4-trifluoromethylacetophenone hydrazone are obtained.

Example (3)

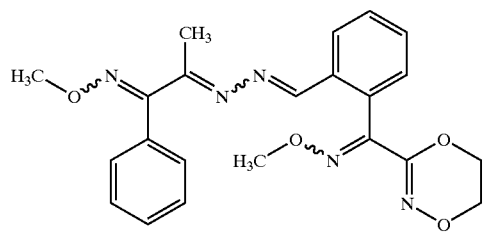

(Process b)

1 g (0.0052 mol) of 2-hydrazono-1-phenylpropan-1-one O-methyl oxime is heated under reflux at the boiling point in 5 ml of ethanol with 1.3 g (0.0052 mol) of 2-[(5,6-dihydro-[1,4,2]dioxazin-3-yl)-methoxyimino-methyl]-benzaldehyde and 5 g of anhydrous magnesium sulphate for 1 hour. The reaction mixture is poured onto water and extracted with diethyl ether, the organic phase is dried over sodium sulphate and the solvent is distilled off in vacuo. The residue is stirred with diethyl ether and the crystals formed are filtered off. The solid is chromatographed over silica gel with diethylether/petroleum ether/methylene chloride (2:1:1). 0.9 g (40.8% of theory) of crystalline 2-({2-[(5,6-dihydro-[1,4,2]dioxazin-3-yl)-methoxyimino-methyl]-benzylidene}-hydrazono)-1-phenylpropan-1-one O-methyl oxime of melting point 136° C. is obtained.

Example (4)

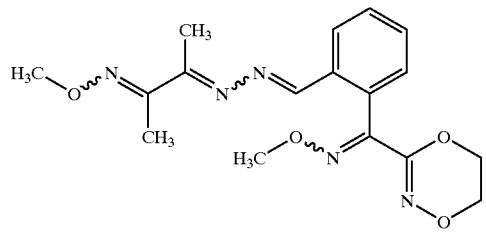

(Process b)

0.5 g (0.0039 mol) of 3-hydrazono-butan-2-one O-methyl oxime is boiled under reflux in 5 ml of ethanol with 0.96 g (0.0039 mol) of 2-[(5,6-dihydro-[1,4,2]dioxazin-3-yl)-methoxyimino-methyl]-benzaldehyde for 2 hours. The reaction mixture is allowed to cool slowly to 20° C. and the crystals are filtered off to give 0.9 g (64.7% of theory) of 3-({2-[(5,6-dihydro-[1,4,2]dioxazin-3-yl)-methoxyiminomethyl]-benzylidene}-hydrazono)-butan-2-one O-methyl oxime.

HPLC: log P=3.17

$^1$H-NMR spectrum (DMSO-d6/TMS): δ=2.05 (3H); 2.14 (3H); 3.81 (3H); 3.97 (3H); 407/4.08/4.10/4.12 (2H); 4.40/4.42/4.43 (2H); 7.21–7.28 (1H); 7.48–7.56 (2H); 7.92–8.05 (1H); 8.10 (1H); ppm.

Preparation of the Starting Substances for Examples (3) and (4)

Example (IV-a-1)

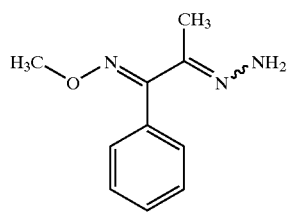

(Process d)

2.5 g (0.014 mol) of 1-phenylpropane-1,2-dione 1-(O-methyl oxime) are heated at 60° C. in 20 ml of ethanol with 1.45 g (0.029 mol) of hydrazine hydrate for 1 hour. The reaction mixture is poured onto water and extracted with diethyl ether, the organic phase is dried over sodium sulphate and the solvent is distilled off in vacuo. The residue is stirred with diethyl ether and the crystals are filtered off. 1.5 g (55.6% of theory) of 2-hydrazono-1-phenylpropan-1-one O-methyl oxime of melting point 132° C. are obtained.

Example (IV-a-2)

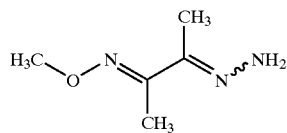

(Process d)

3 g (0.026 mol) of butane-2,3-dione mono-(O-methyl oxime) are heated at 60° C. in 20 ml of ethanol with 2.6 g (0.052 mol) of hydrazine hydrate for 1 hour. The reaction mixture is poured onto water and extracted with diethyl ether, the organic phase is dried over sodium sulphate and the solvent is distilled off in vacuo. The residue is stirred with petroleum ether and the crystals are filtered off. 1 g (29.7% of theory) of 3-hydrazono-butan-2-one O-methyl oxime is obtained.

HPLC: log P=0.97.

$^1$H-NMR spectrum (DMSO-d6/TMS): δ=1.81 (3H); 1.91 (3H); 3.83 (3H); 6.73 (2H, NH$_2$) ppm.

The compounds of the formula (IV-b) according to the invention listed in the following Table 1 are also prepared analogously to Examples (IV-a-1) and (IV-a-2):

TABLE 1

(IV-b)

| Example | Z | $^1$H-NMR | logP |
|---|---|---|---|
| (IV-a-3) | Ethyl | 3.82 (3H); 6.72 (2H) | 1.50 |
| (IV-a-4) | iso-Propyl | 3.79 (3H); 6.60 (2H) | 1.88 |

The compounds of the formula (I-a) according to the invention listed in the following Table 2 are also obtained analogously to Example (1), and in accordance with the general description of the preparation process according to the invention:

TABLE 2

(I-a)

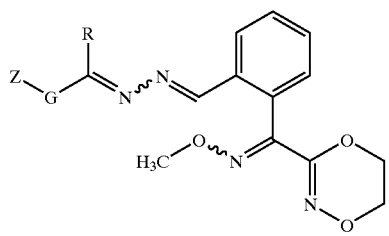

| Example | G | R | Z | logP |
|---|---|---|---|---|
| 5 | — | —CH$_3$ | 4-Ethylphenyl | 3.86 |
| 6 | — | —CH$_3$ | 3-Trifluoromethoxyphenyl | 3.94 |
| 7 | — | —CH$_3$ | 4-Trifluoromethoxyphenyl | |
| 8 | — | —CH$_3$ | 4-Tolyl | 3.46 |

TABLE 2-continued (I-a)

[Structure showing compound with substituents Z-G, R, and fused ring system with H3C-O-N= group and dioxazine ring]

| Example | G | R | Z | logP |
|---------|---|---|---|------|
| 9 | — | —CH₃ | 3-Chlorophenyl | |
| 10 | — | —CH₃ | 4-Chlorophenyl | |
| 11 | — | —CH₃ | 3,4-Dichlorophenyl | |
| 12 | (CH₃)C=N-O-CH₃ | —CH₃ | i-Propyl | 3.92 |
| 13 | (CH₃)C=N-O-CH₃ | —CH₃ | Ethyl | 3.58 |
| 14 | — | —CH₃ | 3-Bromophenyl | 3.75 |
| 15 | — | —CH₃ | 4-Difluoromethoxyphenyl | 3.32 |
| 16 | — | —CH₃ | methyl-benzodioxine-tetrafluoro group | 4.38 |
| 17 | (CH₃)C=N-O-C₂H₅ | —CH₃ | —CH₃ | 3.61 |
| 18 | (CH₃)C=N-O-C₃H₇ | —CH₃ | —CH₃ | 4.08 |

TABLE 2-continued (I-a)

[Structure showing Z-G-C(R)=N-N=CH-phenyl with C(=N-O-CH3)-1,3-dioxazine substituent]

| Example | G | R | Z | logP |
|---------|---|---|---|------|
| 19 | [C(CH3)=N-O-CH2-CH=CH2] | —CH₃ | —CH₃ | 3.71 |
| 20 | [C(CH3)=N-O-C≡CH] | —CH₃ | —CH₃ | 3.20 |
| 21 | [C(CH3)=N-O-CH2-CH=CH-CH3] | —CH₃ | —CH₃ | 4.09 |
| 22 | — | —CH₃ | [3-methyl-1-methyl-1H-indazol-yl] | 3.22 |

Use Examples

Example A

Phytophthora Test (Tomato)/protective

Solvent: 47 parts by weight of acetone

Emulsifier: 3 parts by weight of alkylaryl polyglycol ether

To prepare an appropriate formulation of the active compound, 1 part by weight of active compound is mixed with the stated amounts of solvent and emulsifier and the concentrate is diluted with water to the desired concentration.

To test for protective activity, young plants are sprayed with the formulation of the active compound in the stated application amount. After the spray coating has dried on, the plants are inoculated with an aqueous spore suspension of *Phytophthora infestans*. The plants are then placed in an incubation cabin at about 20° C. and 100% relative atmospheric humidity.

Evaluation is carried out 3 days after the inoculation. In this evaluation, 0% means a degree of action which corresponds to that of the control, while a degree of action of 100% means that no infestation is observed.

In this test, the substances according to the invention described in Examples (1), (14), (15) and (17) show a degree of action of up to 91% or more at an application amount of 100 g/hectare.

TABLE A

Phytophthora test (tomato)/protective

| Active compound | Application amount of active compound in g/hectare | Degree of action in % |
|---|---|---|
| according to the invention: | | |
| 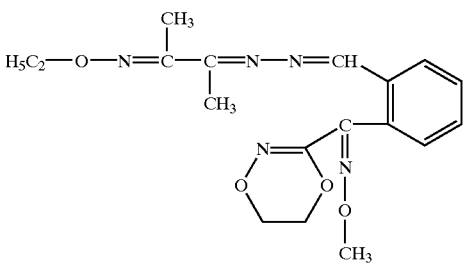 (17) | 100 | 85 |
| 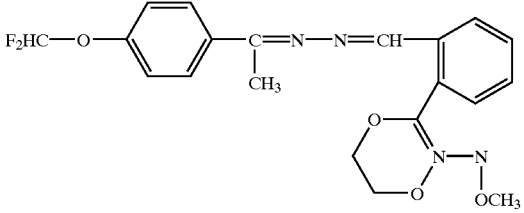 (15) | 100 | 91 |
| 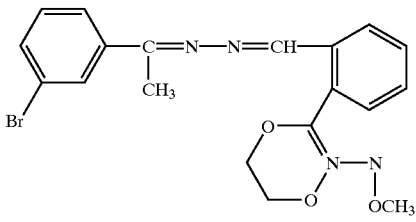 (14) | 100 | 87 |

Example B
Plasmopara Test (Vine)/protective

Solvent: 47 parts by weight of acetone
Emulsifier: 3 parts by weight of alkylaryl polyglycol ether To prepare an appropriate formulation of the active compound, 1 part by weight of active compound is mixed with the stated amounts of solvent and emulsifier and the concentrate is diluted with water to the desired concentration.

To test for protective activity, young plants are sprayed with the formulation of the active compound in the stated application amount. After the spray coating has dried on, the plants are inoculated with an aqueous spore suspension of *Plasmopara viticola* and then remain in an incubation cabin at about 20° C. and 100% relative atmospheric humidity for 1 day. The plants are then placed in a greenhouse at about 21° C. and about 90% relative atmospheric humidity for 5 days. The plants are then moistened and placed in an incubation cabin for 1 day.

Evaluation is carried out 6 days after the inoculation. In this evaluation, 0% means a degree of action which corresponds to that of the control, while a degree of action of 100% means that no infestation is observed.

In this test, the substances according to the invention described in Examples (1), (4), (5), (7), (8), (12) and (13) show a degree of action of up to 100% at an application amount of 100 g/hectare.

TABLE B
Plasmopara test (vine)/protective
| Active compound | Application amount of active compound in g/hectare | Degree of action in % |
|---|---|---|
| according to the invention: | | |
| (4) 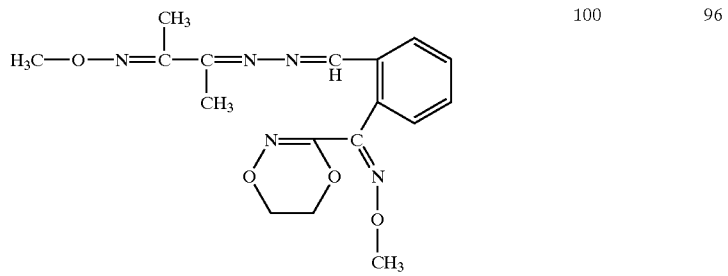 | 100 | 96 |
| (12) 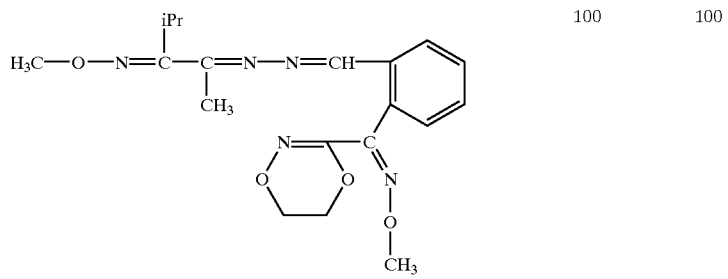 | 100 | 100 |
| 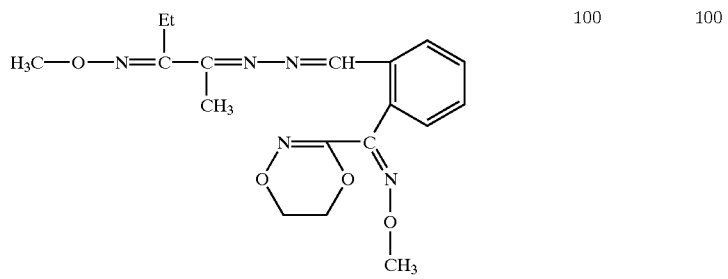 | 100 | 100 |

TABLE B-continued

Plasmopara test (vine)/protective

| Active compound | Application amount of active compound in g/hectare | Degree of action in % |
|---|---|---|
| (13) 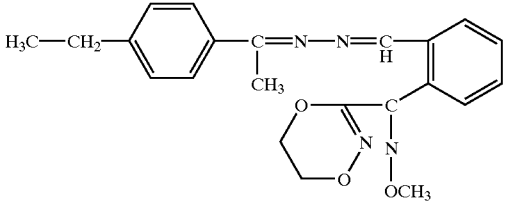 | 100 | 98 |
| (5) 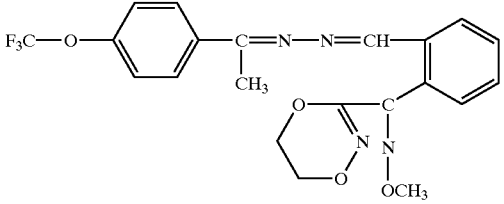 | 100 | 100 |
| (7) 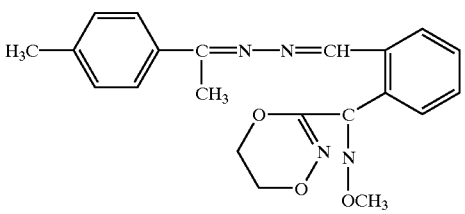 | 100 | 99 |

(8)

Example C

Pyricularia Test (Rice)/protective

Solvent: 2.5 parts by weight of acetone

Emulsifier: 0.06 part by weight of alkylaryl polyglycol ether

To prepare an appropriate formulation of the active compound, 1 part by weight of active compound is mixed with the stated amount of solvent and the concentrate is diluted with water and the stated amount of emulsifier to the desired concentration.

To test for protective activity, young rice plants are sprayed with the formulation of the active compound in the stated application amount. After the spray coating has dried on, the plants are inoculated with an aqueous spore suspension of *Pyricularia oryzae*. The plants are then placed in a greenhouse at 100% relative atmospheric humidity and 25° C.

Evaluation is carried out 4 days after the inoculation. In this evaluation, 0% means a degree of action which corresponds to that of the control, while a degree of action of 100% means that no infestation is observed.

In this test, the substance according to the invention described in Example (1) shows a degree of action of 85% or more at an application amount of 750 g/hectare.

TABLE C

Pyricularia test (rice)/protective

| Active compound | Application amount of active compound in g/hectare | Degree of action in % |
|---|---|---|
| according to the invention: | | |
|  (1) | 750 | 90 |

Example D
Leptosphaeria nodorum Test (Wheat)/protective
Solvent: 25 parts by weight of N,N-dimethylacetamide
Emulsifier: 0.6 part by weight of alkylaryl polyglycol ether
To prepare an appropriate formulation of the active compound, 1 part by weight of active compound is mixed with the stated amounts of solvent and emulsifier and the concentrate is diluted with water to the desired concentration.

To test for protective activity, young plants are sprayed with the formulation of the active compound in the stated application amount. After the spray coating has dried on, the plants are sprayed with a spore suspension of *Leptosphaeria nodorum*. The plants remain in an incubation cabin at 20° C. and 100% relative atmospheric humidity for 48 hours.

The plants are placed in a greenhouse at a temperature of about 15° C. and a relative atmospheric humidity of 80%.

Evaluation is carried out 10 days after the inoculation. In this evaluation, 0% means a degree of action which corresponds to that of the control, while a degree of action of 100% means that no infestation is observed.

In this test, the substance according to the invention described in Example (1) shows a degree of action of 95% or more at an application amount of 250 g/hectare.

TABLE D

Leptosphaeria nodorum test (wheat)/protective

| Active compound | Application amount of active compound in g/hectare | Degree of action in % |
|---|---|---|
| according to the invention: | | |
| (1) (same structure as above) | 250 | 100 |

Example E
Puccinia Test (Wheat)/protective
Solvent: 25 parts by weight of N,N-dimethylacetamide
Emulsifier: 0.6 part by weight of alkylaryl polyglycol ether
To prepare an appropriate formulation of the active compound, 1 part by weight of active compound is mixed with the stated amounts of solvent and emulsifier and the concentrate is diluted with water to the desired concentration.

To test for protective activity, young plants are sprayed with the formulation of the active compound in the stated application amount. After the spray coating has dried on, the plants are sprayed with a conidia suspension of *Puccinia* recondita. The plants remain in an incubation cabin at 20° C. and 100% relative atmospheric humidity for 24 hours.

The plants are then placed in a greenhouse at a temperature of about 20° C. and a relative atmospheric humidity of 80% in order to promote the development of rust pustules.

Evaluation is carried out 10 days after the inoculation. In this evaluation, 0% means a degree of action which corresponds to that of the control, while a degree of action of 100% means that no infestation is observed.

In this test, the substance according to the invention described in Example (1) shows a degree of action of 95% or more at an application amount of 250 g/hectare.

with the stated amounts of solvent arid emulsifier and the concentrate is diluted with water to the desired concentration.

To test for protective activity, young plants are sprayed with the formulation of the active compound in the stated application amount. After the spray coating has dried on, the plants are sprayed with a conidia suspension of *Fusarium nivale* (var. *nivale*).

The plants are placed in a greenhouse under translucent incubation hoods at a temperature of about 15° C. and a relative atmospheric humidity of about 100%.

TABLE E

Puccinia test (wheat)/protective

| Active compound | Application amount of active compound in g/hectare | Degree of action in % |
|---|---|---|
| according to the invention: | | |
| (1) [structure] | 250 | 100 |

Example F

*Fusarium nivale* (var. *nivale*) Test (Wheat)/protective

Solvent: 25 parts by weight of N,N-dimethylacetamide
Emulsifier: 0.6 part by weight of alkylaryl polyglycol ether To prepare an appropriate formulation of the active compound, 1 part by weight of active compound is mixed Evaluation is carried out 4 days after the inoculation. In this evaluation, 0% means a degree of action which corresponds to that of the control, while a degree of action of 100% means that no infestation is observed.

In this test, the substance according to the invention described in Example (1) shows a degree of action of 95% or more at an application amount of 250 g/hectare.

TABLE F

*Fusarium nivale (var. nivale)* test (wheat)/protective

| Active compound | Application amount of active compound in g/ha | Degree of action in % |
|---|---|---|
| according to the invention: | | |
| (1) [structure] | 250 | 100 |

Example G

Venturia Test (Apple)/protective

Solvent: 47 parts by weight of acetone

Emulsifier: 3 parts by weight of alkylaryl polyglycol ether

To prepare an appropriate formulation of the active compound, 1 part by weight of active compound is mixed with the stated amounts of solvent and emulsifier and the concentrate is diluted with water to the desired concentration.

To test for protective activity, young plants are sprayed with the formulation of the active compound in the stated application amount. After the spray coating has dried on, the plants are inoculated with an aqueous conidia suspension of the apple scab causative organism *Venturia inaequalis* and then remain in an incubation cabin at about 20° C. and 100% relative atmospheric humidity for 1 day.

The plants are then placed in a greenhouse at about 21° C. and a relative atmospheric humidity of about 90%.

Evaluation is carried out 12 days after the inoculation. In this evaluation, 0% means a degree of action which corresponds to that of the control, while a degree of action of 100% means that no infestation is observed.

In this test, the substances described in Examples (4), (5), (12), (13), (14) and (15) show a degree of action of up to 100% at an application amount of 10 g/hectare.

TABLE G

| | Venturia test (apple)/protective | |
|---|---|---|
| Active compound | Application amount of active compound in g/ha | Degree of action in % |
| according to the invention: | | |
| 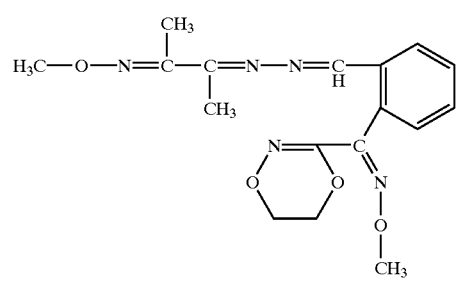 (4) | 10 | 100 |
| 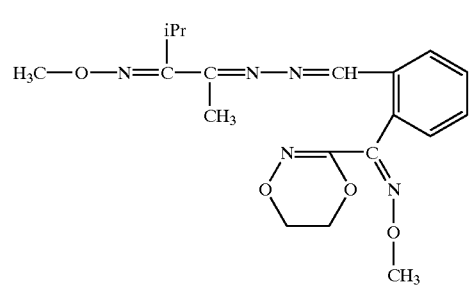 (12) | 10 | 100 |
| 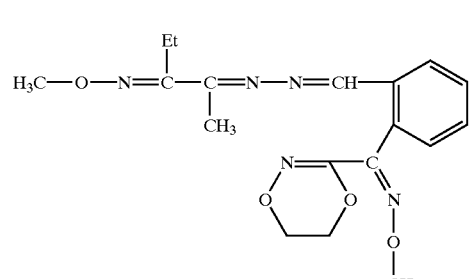 | 10 | 100 |

TABLE G-continued

Venturia test (apple)/protective

| Active compound | Application amount of active compound in g/ha | Degree of action in % |
|---|---|---|
| (13) | 10 | 97 |
| (5) | 10 | 93 |
| (15) | 10 | 100 |
| (14) | 40 | |

What is claimed is:

1. A compound having the formula (I)

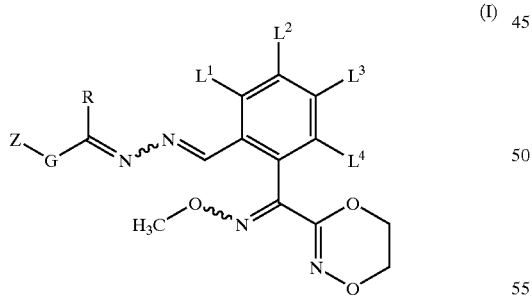

in which

G represents a single bond or a grouping

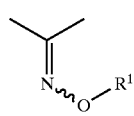

wherein

R¹ represents hydrogen, or represents alkyl having 1 to 6 carbon atoms, alkenyl having 2 to 6 carbon atoms or alkinyl having 2 to 6 carbon atoms, in each case optionally substituted by halogen or alkoxy having 1 to 4 carbon atoms, or represents cycloalkyl which has 3 to 8 carbon atoms and is optionally substituted by halogen, alkyl or alkoxy having in each case 1 to 4 carbon atoms, or represents arylalkyl which has 1 to 4 carbon atoms in the alkyl part and is optionally substituted in the aryl part, the substituents being chosen from the following list:

halogen, cyano, nitro, formyl, carbamoyl, thiocarbamoyl, in each case straight-chain or branched alkyl, alkoxy, alkylthio, alkylsulphinyl or alkylsulphonyl having in each case 1 to 6 carbon atoms, in each case straight-chain or branched alkenyl, alkenyloxy or alkinyloxy having in each case 2 to 6 carbon atoms, in each case straight-chain or branched halogenoalkyl, halogenoalkoxy, halogenoalkylthio, halogenalkylsulphinyl or halogenoalkylsulphonyl having in each case 1 to 6 carbon atoms and 1 to 13 identical or different halogen atoms, in each case straight-chain or branched halogenoalkenyl or halogenoalkenyloxy having in each case 2 to 6 carbon atoms and 1 to 11 identical or different halogen atoms, in each case straight-chain or branched alkylamino, dialkylamino, alkylcarbonyl, alkylcarbonyloxy, alkoxycarbonyl, alkylsulphonyloxy, hydroximinoalkyl or alkoximinoalkyl having in each case 1 to 6 carbon atoms in the individual alkyl parts, in each case divalent alkylene or dioxyalkylene which has in each case 1 to 6 carbon atoms and is in each case optionally monosubstituted or polysubstituted in an identical or different manner by halogen and/or straight-chain or branched alkyl having 1 to 4 carbon atoms and/or straight-chain or branched halogenoalkyl having 1 to 4 carbon atoms and 1 to 9 identical or different halogen atoms, R represents alkyl having 1 to 4 carbon atoms, or cycloalkyl which has 3 to 6 carbon atoms and is optionally mono- to tetrasubstituted by halogen or alkyl, Z represents alkyl or halogenoalkyl which has in each case 1 to 4 carbon atoms and is in each case optionally monosubstituted by cyano or alkoxy;

represents cycloalkyl or cycloalkylalkyl which has in each case 3 to 7 carbon atoms in the cycloalkyl part and 1 to 4 carbon atoms in the alkyl part and is in each case optionally monosubstituted to tetrasubstituted by halogen or alkyl;

represents heterocyclyl or heterocyclylalkyl which has in each case 3 to 7 ring members and 1 to 4 carbon atoms in the alkyl part and is optionally substituted by halogen or alkyl having 1 to 4 carbon atoms, wherein said heterocyclyl or said heterocyclylalkyl is selected from the group consisting of a saturated cyclic compound, an unsaturated cyclic compound and an aromatic cyclic compound in which at least one ring member is a heteroatom, wherein said heteroatom is selected from the group consisting of oxygen, nitrogen and sulfur with the proviso that where said cyclic compound contains more than one oxygen atom said oxygen atoms are not adjacent, and optionally wherein said cyclic compound forms a polycyclic ring system, optionally with additional cyclic compounds selected from the group consisting of carbocyclic and heterocyclic compounds, wherein said additional heterocyclic compounds are as defined above, and wherein said polycyclic ring system includes rings selected from the group consisting of fused-on and bridged rings, said polycyclic ring system preferably being selected from the group consisting of mono-ring aromatic ring systems and bicyclic aromatic ring systems;

or represents aryl or arylalkyl which has in each case 6 to 10 carbon atoms in the aryl part and 1 to 4 carbon atoms in the alkyl part and is in each case optionally monosubstituted to tetrasubstituted in an identical or different manner in the aryl part, the possible substituents preferably being chosen from the following list:

halogen, cyano, nitro, amino, formyl, carbamoyl, thiocarbamoyl;

in each case straight-chain or branched alkyl, alkoxy, alkoxyalkyl, alkylthioalkyl, alkylaminoalkyl, dialkylaminoalkyl, alkylthio, alkylsulphinyl or alkylsulphonyl having in each case 1 to 8 carbon atoms;

in each case straight-chain or branched alkenyl or alkenyloxy having in each case 2 to 6 carbon atoms;

in each case straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms;

in each case straight-chain or branched halogenoalkenyl or halogenoalkenyloxy having in each case 2 to 6 carbon atoms and 1 to 11 identical or different halogen atoms;

in each case straight-chain or branched alkylamino, dialkylamino, alkylcarbonyl, alkylaminocarbonyl, diakylaminocarbonyl, arylakylaminocarbonyl, alkenylcarbonyl or alkinylcarbonyl having 1 to 6 carbon atoms and in the particular hydrocarbon chains;

cycloalkyl or cycloalkyloxy having in each case 3 to 6 carbon atoms;

in each case divalent alkylene having 3 or 4 carbon atoms, oxyalkylene having 2 or 3 carbon atoms or dioxyalkylene having 1 or 2 carbon atoms, in each case optionally monosubstituted to tetrasubstituted in an identical or different manner by fluorine, chlorine, oxo, methyl, trifluoromethyl or ethyl;

or a grouping

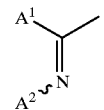

wherein $A^1$ represents hydrogen or alkyl having 1 to 4 carbon atoms or cycloalkyl having 3 to 6 carbon atoms and $A^2$ represents hydroxyl, amino, methylamino, methyl, phenyl, benzyl, alkoxy, alkylamino or dialkylamino having 1 to 4 carbon atoms in the particular alkyl chains and $L^1, L^2, L^3$ and $L^4$ are identical or different and independently of one another in each case represent hydrogen, halogen, cyano, nitro or in each case optionally halogen-substituted alkyl, alkoxy, alkylthio, alkylsulphinyl or alkylsulphonyl having in each case 1 to 6 carbon atoms and in each case optionally substituted by 1 to 5 halogen atoms.

2. The compound of the formula (I) according to claim 1, in which

G represents a single bond.

3. The compound of the formula (I) according to claim 1, in which

G represents a grouping

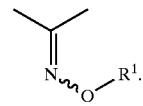

4. The compounds of the formula (I) according to claim 1, in which

R represents methyl, ethyl, n- or i-propyl, or represents cyclopropyl, cyclobutyl or cyclopentyl, in each case optionally monosubstituted to tetrasubstituted by fluorine, chlorine, methyl or ethyl, in particular represents methyl.

5. The compounds of the formula (I) according to claim 1, in which

G represents a single bond and
Z represents cyclopentyl or cyclohexyl, in each case optionally monosubstituted to tetrasubstituted by fluorine, chlorine, methyl or ethyl;
represents thienyl, pyridyl, furyl, thienylmethyl, pyridylmethyl, benzopyrazolyl or furylmethyl, optionally substituted by methyl, ethyl, fluorine, chlorine or bromine;
or represents benzyl, 1-phenylethyl or 2-phenylethyl, in each case optionally monosubstituted to tetrasubstituted in an identical or different manner, in particular substituted phenyl, the possible substituents preferably being chosen from the following list:
fluorine, chlorine, bromine, cyano, nitro, amino, formyl, carbamoyl, thiocarbamoyl, methyl, ethyl, n- or i-propyl, n-, i-, s- or t-butyl, methoxymethyl, methoxy, ethoxy, n- or i-propoxy, methylthio, ethylthio, n- or i-propylthio, methylsulphinyl, ethylsulphinyl, methylsulphonyl or ethylsulphonyl, methylaminomethyl, dimethylaminomethyl, vinyl, allyl, 2-methylallyl, propen-1-yl, crotonyl, propargyl, vinyloxy, allyloxy, 2-methylallyloxy, propen-1-yloxy, crotonyloxy, propargyloxy;
trifluoromethyl, trifluoroethyl, difluoromethoxy, trifluoromethoxy, difluorochloromethoxy, trifluoroethoxy, pentafluoroethoxy, 2-chloro-1,1,2-trifluoroethoxy, difluoromethylthio, trifluoromethylthio, difluorochloromethylthio, trifluoromethylsulphinyl or trifluoromethylsulphonyl, methylamino, ethylamino, n- or i-propylamino, dimethylamino, diethylamino, acetyl, propionyl, methoxycarbonyl, ethoxycarbonyl, methylaminocarbonyl, ethylaminocarbonyl, dimethylaminocarbonyl, diethylaminocarbonyl, acryloyl, propioloyl, cyclopentyl, cyclohexyl, or in each case divalent propanediyl, ethyleneoxy, methylenedioxy or ethylenedioxy, in each case optionally monosubstituted to tetrasubstituted in an identical or different manner by fluorine, chlorine, oxo, methyl or trifluoromethyl, or a grouping

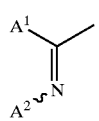

wherein
$A^1$ represents hydrogen or methyl and
$A^2$ represents hydroxyl, methoxy, ethoxy, amino, methylamino, methyl, phenyl or benzyl.

6. The compounds of the formula (I) according to claim 1, in which
G represents the grouping

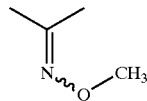

and
Z represents methyl, ethyl, n- or i-propyl, n-, i-, s- or t-butyl or trifluoromethyl, or represents cyclopentyl or cyclohexyl, in each case optionally monosubstituted to tetrasubstituted by fluorine, chlorine, methyl or ethyl;
represents thienyl, pyridyl, furyl, thienylmethyl, pyridylmethyl or furylmethyl, optionally substituted by methyl, ethyl, fluorine, chlorine or bromine;
or represents benzyl, 1-phenylethyl or 2-phenylethyl, in each case optionally monosubstituted to tetrasubstituted in an identical or different manner, in particular substituted phenyl, the possible substituents preferably being chosen from the following list:
fluorine, chlorine, bromine, cyano, nitro, amino, formyl, carbamoyl, thiocarbamoyl, methyl, ethyl, n- or i-propyl, n-, i-, s- or t-butyl, methoxymethyl, methoxy, ethoxy, n- or i-propoxy, methylthio, ethylthio, n- or i-propylthio, methylsulphinyl, ethylsulphinyl, methylsulphonyl or ethylsulphonyl, methylaminomethyl, dimethylaminomethyl, vinyl, allyl, 2-methylallyl, propen-1-yl, crotonyl, propargyl, vinyloxy, allyloxy, 2-methylallyloxy, propen-1-yloxy, crotonyloxy, propargyloxy;
trifluoromethyl, trifluoroethyl, difluoromethoxy, trifluoromethoxy, difluorochloromethoxy, trifluoroethoxy, pentafluoroethoxy, 2-chloro-1,1,2-trifluoroethoxy, difluoromethylthio, trifluoromethylthio, difluorochloromethylthio, trifluoromethylsulphinyl or trifluoromethylsulphonyl, methylamino, ethylamino, n- or i-propylamino, dimethylamino, diethylamino, acetyl, propionyl, methoxycarbonyl, ethoxycarbonyl, methylaminocarbonyl, ethylaminocarbonyl, dimethylaminocarbonyl, diethylaminocarbonyl, acryloyl, propioloyl, cyclopentyl, cyclohexyl, or in each case divalent propanediyl, ethyleneoxy, methylenedioxy or ethylenedioxy, in each case optionally monosubstituted to tetrasubstituted in an identical or different manner by fluorine, chlorine, oxo, methyl or trifluoromethyl, or a grouping

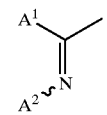

wherein
$A^1$ represents hydrogen or methyl and
$A^2$ represents hydroxyl, methoxy, ethoxy, amino, methylamino, methyl, phenyl or benzyl.

7. The compounds of the formula (I) according to claim 1, in which
$L^1$, $L^2$, $L^3$ and $L^4$ are identical or different and independently of one another in each case represent hydrogen, fluorine, chlorine, bromine, cyano, nitro, methyl, ethyl, n- or i-propyl, n-, i-, s- or t-butyl, methoxy, ethoxy, n- or i-propoxy, methylthio, ethylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, preferably hydrogen or methyl, and in particular hydrogen.

8. The compounds of the formula (I) according to claim 1, in which
G represents a single bond.

9. A fungicidal composition, characterized by a content of at least one compound of the formula (I) according to claim 1.

10. A method of combating fungi comprising the step of applying a fungicidally effective amount of a compound of the formula (I) according to claim 1 to a member selected from the group consisting of said fungi, an environment of said fungi, and combinations thereof.

11. A process for the preparation of compounds of the formula (I) as defined in claim 1 comprising reacting a) ketones of the formula (II)

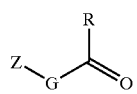

(II)

in which

G, R and Z have the meanings given in claim 1, with an aldehyde of the formula (III)

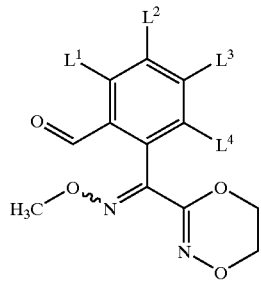

(III)

in which

L$^1$, L$^2$, L$^3$ and L$^4$ have the meanings given in claim 1, and hydrazine or hydrazine hydrate, optionally in the presence of a diluent and optionally in the presence of a catalyst, or reacting b) hydrazones of the formula (IV)

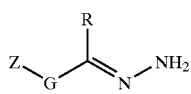

(IV)

in which

G, R and Z have the meanings given in claim 1, are reacted with an aldehyde of the formula (III), optionally in the presence of a diluent and optionally in the presence of a catalyst, or reacting c) hydrazine derivatives of the formula (V)

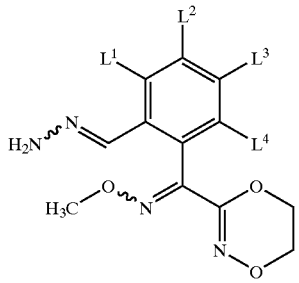

(V)

in which

L$^1$, L$^2$, L$^3$ and L$^4$ have the meanings given in claim 1, with a ketone of the formula (II), optionally in the presence of a diluent and optionally in the presence of a catalyst.

12. A compound having the formula (III)

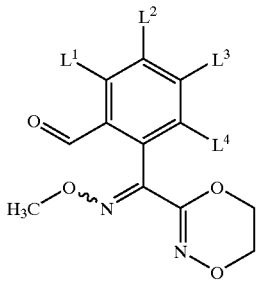

(III)

in which

L$^1$, L$^2$, L$^3$ and L$^4$ have the meanings given in claim 1.

13. A compound having the formula (I) according to claim 1, in which

G represents a grouping

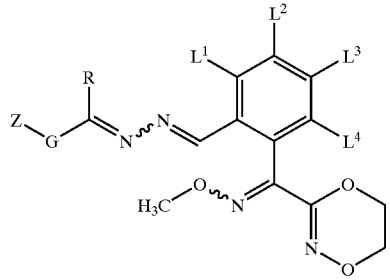

(I)

wherein

R represents hydrogen, methyl, ethyl, n- or i-propyl, n-, i- or s-butyl, allyl, propargyl or but-2-en-1-yl.

14. The compounds of claim 1, wherein L$^1$, L$^2$, L$^3$ and L$^4$ are identical or differently and independently of one another in each case represent hydrogen or methyl.

* * * * *